(12) United States Patent
Aki et al.

(10) Patent No.: US 7,427,511 B2
(45) Date of Patent: Sep. 23, 2008

(54) IMMUNOCHROMATOGRAPHIC TEST DEVICE

(75) Inventors: Masako Aki, Kobe (JP); Shinya Nagai, Akashi (JP); Noriyuki Saito, Akashi (JP); Takeshi Imoarai, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 242 days.

(21) Appl. No.: 11/325,489

(22) Filed: Jan. 5, 2006

(65) Prior Publication Data

US 2006/0154241 A1    Jul. 13, 2006

(30) Foreign Application Priority Data

Jan. 12, 2005    (JP) .............................. 2005-005383

(51) Int. Cl.
   *G01N 33/53*    (2006.01)
(52) U.S. Cl. .................. 436/518; 435/7.1; 435/287.7; 435/287.9; 435/287.8; 435/805; 435/810; 435/970; 422/56; 422/57; 436/514; 436/169; 436/530; 436/805; 436/810
(58) Field of Classification Search ................. 436/518, 436/514, 169, 530, 805, 810; 435/7.1, 805, 435/287.7, 287.8, 287.9, 810, 970; 422/56, 422/57
See application file for complete search history.

(56) References Cited

U.S. PATENT DOCUMENTS

| 4,943,522 | A | * | 7/1990 | Eisinger et al. | ............. 435/7.25 |
| 5,126,276 | A | * | 6/1992 | Fish et al. | .................... 436/531 |
| 5,356,782 | A | * | 10/1994 | Moorman et al. | ............ 435/7.9 |
| 5,559,041 | A | * | 9/1996 | Kang et al. | ................. 436/518 |
| 6,534,324 | B1 | * | 3/2003 | Zin | ............................. 436/518 |

FOREIGN PATENT DOCUMENTS

JP    2003-344406 A    12/2003

* cited by examiner

*Primary Examiner*—Bao-Thuy L Nguyen
(74) *Attorney, Agent, or Firm*—Sughrue Mion, PLLC

(57) ABSTRACT

An immunochromatographic test device of the present invention comprises: a sample receiving member for receiving a sample; a label holding member for holding a labeling substance to bind to an analyte contained in the sample; and a chromatographic membrane having a detection zone at which an immobilization substance to bind to the analyte is immobilized, wherein the sample receiving member disposed to cover the label holding member and in contact with the chromatographic membrane, and the chromatographic membrane is spaced apart from the label holding member.

18 Claims, 3 Drawing Sheets

IMMUNOCHROMATOGRAPHIC TEST DEVICE

CROSS-REFERENCE TO RELATED APPLICATION

This application is related to Japanese application No. 2005-5383 filed on Jan. 12, 2005, whose priority is claimed and the disclosure of which is incorporated by reference in its entirety.

TECHNICAL FIELD

The present invention relates to an immunochromatographic test device.

BACKGROUND

Immunochromatography can be utilized to perform tests of various diseases simply and easily.

Because an analyte in a specimen is usually a slightly-existing substance, such as an influenza virus, HBs antigen or the like, there are demands for enhancement of sensitivity of immunochromatographic tests. Also, there are demands for a test device that permits rapid detection of an analyte in a specimen.

Conventional test devices, however, have a problem that a long time is required for the elution of a labeling substance from a label holding member and thus for obtaining test results.

SUMMARY

The present invention has been made in view of these circumstances, and in one aspect, the present invention is to provide an immunochromatographic test device that permits rapid yield of test results.

In one aspect, the present invention provides an immunochromatographic test device comprising: a sample receiving member for receiving a sample; a label holding member for holding a labeling substance to bind to an analyte contained in the sample; and a chromatographic membrane (a membrane for chromatography) having a detection zone at which an immobilization substance to bind to the analyte is immobilized, wherein the sample receiving member disposed to cover the label holding member and in contact with the chromatographic membrane, and the chromatographic membrane is spaced apart from the label holding member.

In another aspect, the present invention provides an immunochromatographic test device comprising: a sample receiving member for receiving a sample; a label holding member for holding a labeling substance to bind to an analyte contained in the sample; a chromatographic membrane having a detection zone at which an immobilization substance to bind to the analyte is immobilized; and a development member, wherein the label holding member is disposed in contact with the sample receiving member, the chromatographic membrane is spaced apart from the label holding member, and the development member is disposed in contact with the label holding member and the chromatographic membrane.

The present inventors have found that providing the development member or the sample receiving member between the label holding member and the chromatographic membrane will increase the rate of elution of the labeling substance from the label holding member, and will provide an immunochromatographic test device that permits a highly sensitive test and rapid yield of test results.

According to the present invention, due to enhancement of the rate of elution of the labeling substance from the label holding member, immunochromatographic test results can be obtained rapidly.

DESCRIPTION OF THE PREFERRED EMBODIMENTS

Figure 6:
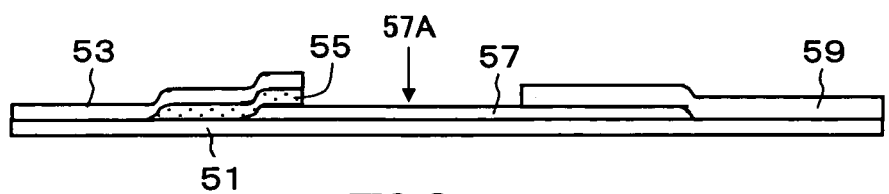
FIG. 6 is a cross sectional view showing a conventional immunochromatographic test device.

Referring to FIG. 6, a conventional immunochromatographic test device described in Japanese Unexamined Patent Publication No. 2003-344406, for example will be described.

The conventional immunochromatographic test device comprises a sample receiving member 53, an impregnated member 55, a chromatographic membrane 57, and an absorption member 59, all provided on an adhesive sheet 51. The impregnated member 55 is impregnated with an antibody labeled with latex particles. The antibody binds to an antigen, which is an analyte, thereby to form a complex. The chromatographic membrane 57 includes a capturing site 57A, which is in the form of a line. The site carries an antibody to bind to the antigen, which is the analyte.

The principle of immunochromatography will be briefly described. A sample is prepared by diluting a specimen such as a body fluid with a development solvent. When being dripped onto the sample receiving member 53, the sample moves into the impregnated member 55 by capillarity. At the impregnated member 55, the antibody labeled with the latex particles elutes into the development solvent. If the sample contains the antigen, which is analyte, the antibody binds to the antigen by an antigen-antibody reaction to form a complex. Then, the sample moves to the capturing site 57A of the chromatographic membrane 57 by capillarity. At the capturing site 57A, the antigen is captured by the antibody carried at the capturing site 57A by an antigen-antibody reaction. Since the captured antigen is in the form of the complex with the antibody labeled with the latex particles, a line in color of the latex particles appears at the capturing site 57A. Thus, by visual observation of the colored line, the presence or absence of the analyte in the specimen is judged.

Embodiments of the present invention will be described referring to the drawings. The drawings are given only for an illustrative purpose. The present invention should not be construed as being limited to the embodiments shown in the drawings.

1. First Embodiment

Figure 1:
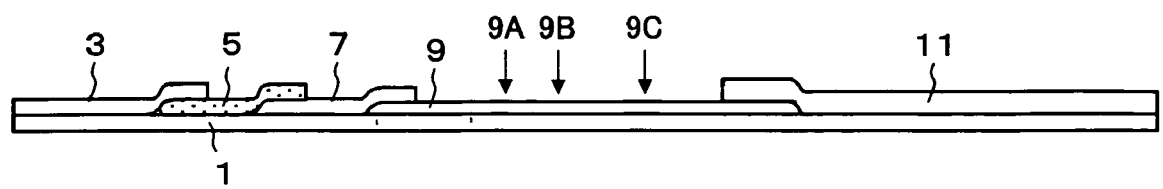
FIG. 1 is a cross sectional view showing an immunochromatographic test device of a first embodiment of the present invention.

FIG. 1 is a cross sectional view showing an immunochromatographic test device according to a first embodiment of the present invention. The immunochromatographic test device comprises a sample receiving member 3 made of a nonwoven rayon fabric, a label holding member 5 made of a nonwoven glass fiber fabric, a development member 7 made of a nonwoven rayon fabric, a chromatographic membrane 9 made of a porous material of nitrocellulose, and an absorption member 11 made of a nonwoven cellulose fabric, all provided on a substrate 1 made of a plastic plate having an adhesive layer on a surface of the substrate 1. The label holding member 5 is disposed in contact with the sample receiving member 3 and holds labeling substances to bind to analytes contained in a sample by antigen-antibody reactions. The chromatographic membrane 9 is spaced apart from the label holding member. The chromatographic membrane 9 has detection zones at which immobilization substances to bind to the analytes by antigen-antibody reactions are immobilized. The development member 7 is disposed in contact with the label holding member 5 and the chromatographic membrane 9. The absorption member 11 is disposed in contact with the chromatographic membrane 9.

The chromatographic membrane 9 has, in the order of upstream to down stream, a first detection zone 9A, a second detection zone 9B and a control zone 9C each in the form of a line. The label holding member 5 holds a first labeling substance, a second labeling substance and a control labeling substance. At the first detection zone 9A, an anti-influenza A virus antibody (hereafter, referred to as "anti-flu A antibody") is immobilized. At the second detection zone 9B, an anti-influenza B virus antibody (hereafter, referred to as "anti-flu B antibody") is immobilized. At the control zone 9C, biotin is immobilized. The first labeling substance is an anti-flu A antibody labeled with a blue latex particle. The second labeling substance is an anti-flu B antibody labeled with a blue latex particle. The control labeling substance is avidin labeled with a red latex particle. The anti-flu A antibody binds to an influenza A virus (hereafter, referred to as "flu A virus"), which is a first analyte, by an antigen-antibody reaction. The anti-flu B antibody binds to an influenza B virus (hereafter, referred to as "flu B virus"), which is a second analyte, by an antigen-antibody reaction.

In the case of the anti-flu A antibody for example, if the sample contains the flu A virus, the labeled anti-flu A antibody at the label holding member 5 recognizes a specific site of the flu A virus and binds to the flu A virus to form a complex by an antigen-antibody reaction. Then, the anti-flu A antibody at the chromatographic membrane 9 recognizes another site of the flu A virus and captures the complex. When the complex is captured, a blue line appears at the first detection zone 9A. Thus, the presence of the flu A virus is confirmed by visual observation.

The avidin is not captured by either the anti-flu A antibody or by the anti-flu B antibody present at the chromatographic membrane 9, but it binds specifically to biotin and thus is captured by the biotin immobilized at the control zone 9C. When the avidin is captured, a red line appears at the control zone 9C so that it is confirmed by visual observation that the avidin arrives at the control zone 9C. Since the control zone 9C is located downstream of the first detection zone 9A and the second detection zone 9B, appearance of the red line indicates the completion of passage of the sample through the first detection zone 9A and the second detection zone 9B.

The use of the test device according to the present embodiment provides immunochromatographic test results quickly. Now the principle will be explained.

A sample is prepared by diluting a specimen such as a fluid sucked from a nasal cavity of a patient with a development solvent. When being dripped onto the sample receiving member 3, the sample moves by capillarity through the label holding member 5, through the development member 7 and through the chromatographic membrane 9 in sequence to reach the absorption member 11. During the passage of the sample through the label holding member 5, the labeling substance held at the label holding member 5 elutes into the development solvent. According to the present embodiment, the development member 7 is provided between the label holding member 5 and the chromatographic membrane 9 to increase the rate of elution.

Figure 2A:
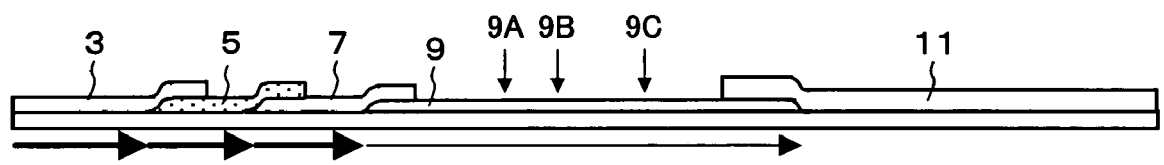
FIGS. 2A and 2B are cross sectional views for a comparison between the rates of development of a sample in the presence of a development member (FIG. 2A) and in the absence of it (FIG. 2B), to explain the principle of the present invention.
Figure 2B:
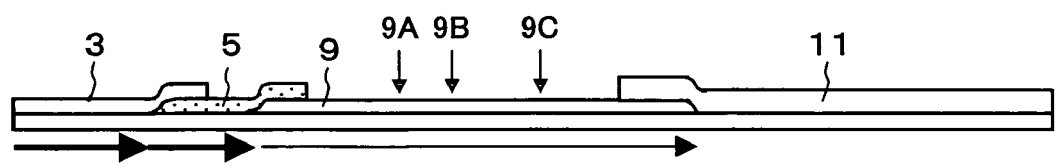

Referring to FIGS. 2A and 2B, the rates of development of the sample in the presence of the development member 7 (FIG. 2A) and in the absence of it (FIG. 2B) will be compared. FIGS. 2A and 2B correspond to the test device according to the present invention and a conventional one. In FIGS. 2A and 2B, the sample receiving member 3, the label holding member 5 and the development member 7 each are made of rayon or a nonwoven glass fiber fabric, and thus these members quickly absorb the sample, so that the sample quickly develops. The chromatographic membrane 9, on the other hand, is made of a porous material of nitrocellulose, and thus the chromatographic membrane 9 slowly absorbs the sample, so that the sample slowly develops. The width of each arrow in FIGS. 2A and 2B shows a schematic representation of the rate of development of the sample at each member.

First, referring to FIG. 2B, the sample dripped onto the sample receiving member 3 quickly develops within the sample receiving member 3 and the label holding member 5, but when the sample arrives at the chromatographic membrane 9, the rate of development is slowed, so that the sample stagnates within the label holding member 5.

Next, referring to FIG. 2A, the sample dripped onto the sample receiving member 3 quickly develops within the sample receiving member 3 and the label holding member 5 and also quickly within the development member 7 without stagnating within the label holding member 5 (that is, the sample quickly moves through the label holding member 5). Since the sample quickly moves through the label holding member 5, the labeling substances held at the label holding member 5 quickly elutes into the development solvent (this situation continues at least until the development member 7 is sufficiently filled with the sample). The rapid elution of the labeling substances hastens appearance of the lines at the detection zones. Thus, the use of the test device according to the present embodiment provides immunochromatographic test results quickly.

Although the particular embodiment of the present invention has been described, it is to be understood that the present invention is not limited to the embodiment and that various changes and modifications are possible.

The substance to be detected is not particularly limited as long as it is a substance that undergoes an antigen-antibody reaction. Examples of such substances include cells such as bacteria, protista and mycete; viruses; proteins; and polysaccharides. Further examples include the aforementioned influenza viruses; parainfluenza virus; RS virus; *Mycoplasma pneumoniae*; rotavirus; calcivirus; coronavirus; adenovirus; enterovirus; herpesvirus; human immunodeficiency virus; hepatitis virus; pathogenic viruses causing Sever Acute Respiratory Syndrome; *Escherichia coli; Staphyllococcus aueus; Streptococcus pneumoniae; Streptococcus pyogenes;* malaria parasite; and others; pathogens causing various diseases such as digestive system disease, central nervous system diseases, and hemorrhagic fever; metabolites of these; tumor markers such as carcinoembryonic antigen and CYFRA; and hormones.

The substrate 1 is provided for properly supporting the above members such as the sample receiving member 3 and the label holding member 5. For the substrate, various materials such as paper and glass are usable in addition to plastics. For the sample receiving member 3, various materials such as a glass fiber and cellulose are usable in addition to rayon. For the label holding member 5, various materials such as a cellulose fiber are usable in addition to a glass fiber. For the development member 7, various materials such as a glass fiber and a cellulose fiber are usable in addition to rayon. For the chromatographic membrane 9, various materials such as nylon (e.g., modified nylon having introduced therein a carboxy group or an amino group optionally containing an alkyl group as a substituent), polyvinylidenedifluoride (PVDF) and cellulose acetate are usable in addition to nitrocellulose. For the absorption member 11, various materials such as a glass fiber are usable in addition to cellulose. For the sample receiving member 3, the label holding member 5, the development member 7, the chromatographic membrane 9 and the absorption member 11, materials of various structures permitting development of the sample by capillarity are usable in addition to a nonwoven material and a porous material.

The chromatographic membrane 9 may comprise one or more detection zones. The chromatographic membrane 9 may comprise no control zone. The detection zones and the control zone may be not in the form of a line but in a square or circular form. The label holding member 5 may hold one or more labeling substances. Further, the label holding member 5 may hold no control labeling substance. The labeling substances may be labeled with latex particles in colors other than blue and red, with a metal collide such as gold, or with pigment molecules. The labeling substances may be labeled with fluorescent particles or magnetic particles. In such a case, the presence or absence of an analyte is confirmed not by visual observation but by measurement of fluorescence, magnetic force or the like. In the case where there are two or more labeling substances, the labeling substances may be labeled in different colors or in the same color. Also, the labeling substances and the control labeling substance may be labeled in different colors or in the same color.

For the immobilization substances and the labeling substances, various antibodies and antigens are usable. More specifically, when the analytes are antigens, the immobilization substances and the labeling substances to be used are antibodies to bind to the antigens by antigen-antibody reactions. When the analytes are antibodies, the immobilization substances and the labeling substances to be used are antigens or antibodies to bind to the antibodies by antigen-antibody reactions.

The immobilization substance at the control zone and the control labeling substance may be avidin and biotin, respectively. Further, the immobilization substance at the control zone and the control labeling substance may be other than a combination of biotin and avidin, and may be a combination of substances to bind together by an antigen-antibody reaction. For example, when the control labeling substance is an antigen, the immobilization substance to be used at the control zone is an antibody to bind to the antigen by an antigen-antibody reaction, and vice versa. The control labeling substance to be used is such that does not bind to none of the analytes and none of the immobilization substance present at the detection zone by an antigen-antibody reaction.

2. Second Embodiment

Figure 3:
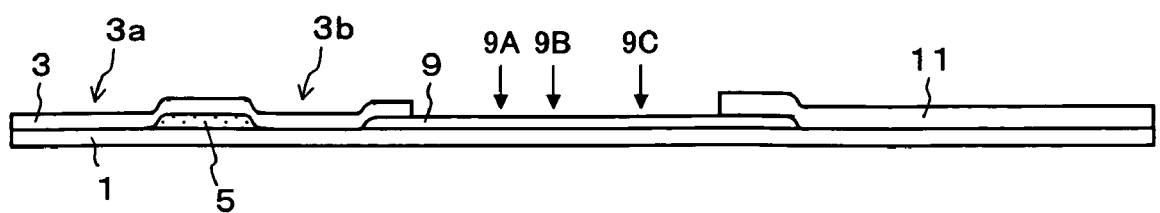
FIG. 3 is a cross sectional view showing an immunochromatographic test device of a second embodiment of the present invention.

FIG. 3 is a cross sectional view showing an immunochromatographic test device of a second embodiment. This test device is identical to that of the first embodiment except that it comprises no development member 7 and that the sample receiving member 3 covers the label holding member 5 and is disposed in contact with the chromatographic membrane 9.

In the second embodiment, an upstream zone 3a of the sample receiving member 3 plays the role of the sample receiving member 3 of the first embodiment, and a downstream zone 3b plays the role of the development member 7 of the first embodiment. When dripped upon the upstream zone 3a of the sample receiving member 3, the same sample as used in the first embodiment moves by capillarity through the label holding member 5, through the downstream zone 3b of the sample receiving member 3 and through the chromatographic membrane 9 in sequence to reach the absorption member 11. Since the downstream zone 3b of the sample receiving member 3 performs the same function as that of the development member 7, the sample quickly moves through the label holding member 5, so that the labeling substances held at the label holding member 5 quickly elute into the development solvent. The rapid elution of the labeling substances hastens appearance of the lines at the detection zones. Thus, the use of the test device according to the present embodiment permits rapid yield of immunochromatographic test results.

EXAMPLE 1

Now Example 1 of the present invention will be explained.

1. Preparation of an Immunochromatographic Test Device (Assay Strip)

Following a procedure described below, a chromatographic membrane and a label holding member were prepared, and by using these members, an immunochromatographic test device was prepared.

1-1. Preparation of a Chromatographic Membrane

Figure 4:
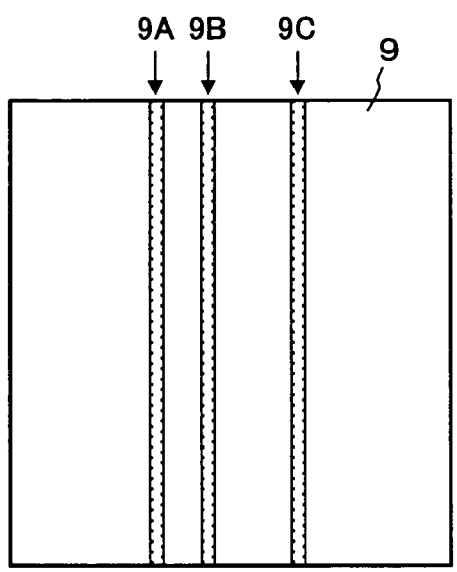
FIG. 4 is a plan view of a chromatographic membrane of Example 1 of the present invention.

As shown in FIG. 4 (a plan view of the chromatographic membrane), an anti-influenza A virus monoclonal antibody diluted with a phosphate buffer solution (pH 7.0) to a concentration of 2.0 mg/mL was applied to the first detection zone 9A of the chromatographic membrane 9 which is made of a nitrocellulose membrane. An anti-influenza B virus monoclonal antibody diluted with a phosphate buffer solution (pH 7.0) to a concentration of 1.5 mg/mL was applied to the first detection zone 9B of the chromatographic membrane 9. Biotin BSA was applied to the control zone 9C of the chromatographic membrane 9. Application to the chromatographic membrane 9 was done by using an antibody application device (manufactured by BioDot Inc.). After the application, the chromatographic membrane was dried at 50° C. for 30 min.

After the drying, the chromatographic membrane 9 was immersed into a blocking solution (phosphate buffer solution, pH 7.0, containing BSA), to be blocked. After the blocking, the chromatographic membrane 9 was washed with a cleaning fluid (phosphate buffer solution, pH 7.0, containing SDS), and then dried at 40° C. for 120 min. Thus, preparation of the chromatographic membrane 9 was completed.

1-2. Preparation of a Label Holding Member

Blue polystyrene latex particles of a diameter of 0.3 µm were conjugated to an anti-influenza A virus monoclonal antibody and suspended in a buffer solution for dispersion (phosphate buffer solution, pH 7.0, containing BSA and sucrose). Thus, preparation of latex particles conjugated to an anti-influenza A virus monoclonal antibody were completed.

Blue polystyrene latex particles of a diameter of 0.3 μm were conjugated to an anti-influenza B virus monoclonal antibody and suspended in a buffer solution for dispersion (phosphate buffer solution, pH 7.0, containing BSA and sucrose). Thus, preparation of the latex particles conjugated to an anti-influenza B virus monoclonal antibody was completed.

Red polystyrene latex particles of a diameter of 0.19 μm were conjugated to streptoavidin and suspended in a buffer solution for dispersion (phosphate buffer solution, pH 7.0, containing BSA and sucrose). Thus, preparation of the latex particles conjugated to streptoavidin were obtained.

The latex particles conjugated to the anti-influenza A virus monoclonal antibody, the latex particles conjugated to the anti-influenza B virus monoclonal antibody and the latex particles conjugated to the streptoavidin were mixed. The mixture of these latex particles was put on a glass fiber pad (832 μL/300 mm×5 mm), followed by drying in a vacuum dryer. Thus, preparation of the label holding member was completed.

1-3. Attachment of Members and Cutting

Figure 5A:
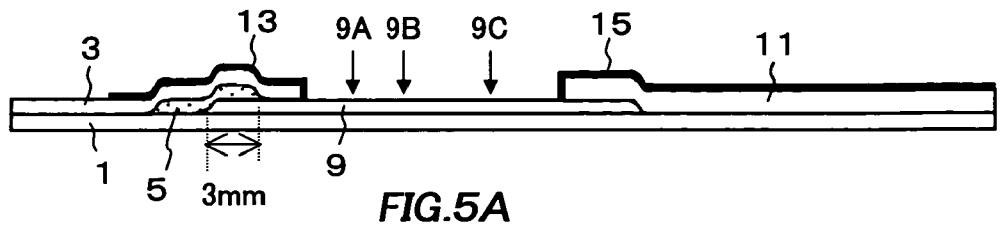
FIGS. 5A to 5C are cross sectional views showing immunochromatographic test devices of Example 1 of the present invention.
Figure 5B:
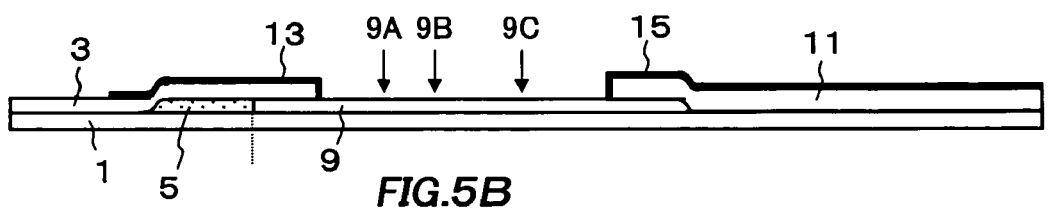
Figure 5C:
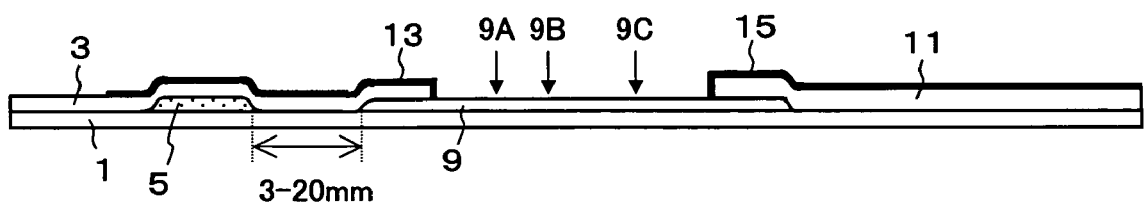

Referring to FIGS. 5A to 5C, attachment of members to a substrate will be explained. FIG. 5A shows an embodiment where the distance between a right end of the label holding member 5 and a left end of the chromatographic membrane 9 is −3 mm (that is, there is a 3-mm overlap between them). FIG. 5B shows an embodiment where the distance between the right end of the label holding member 5 and the left end of the chromatographic membrane 9 is 0 mm (that is, the two ends are at the same location). FIG. 5C shows embodiments where the distances between the right end of the label holding member 5 and the left end of the chromatographic membrane 9 are 3, 5, 10 and 20 mm. Table 1 shows widths (lengths in the direction of a sample flow) of the members in each embodiment.

2. Tests

Next, using the test devices prepared above, tests were conducted on the time required for detection of the analytes.

(1) First, an influenza A virus (cultured virus: A/New Caledonia/20/99) was diluted 160 times with a physiological salt solution to a virus concentration of $1.8 \times 10^6$ FFU/mL. Next, an influenza B virus (cultured virus: B/Shandong/7/97) was diluted 80 times with a physiological salt solution to a virus concentration of $3.5 \times 10^5$ FFU/mL. The term "FFU (focus forming unit)" refers to the number of viruses decided by immunostaining cells infected with the virus and counting the immunostained cells.

(2) Next, 150 μL of the solution obtained in (1) above by diluting the influenza A virus was added to 800 μL of an analyte extracting reagent (phosphate buffer solution, pH 7.30, containing 0.3 w/v % NP-40 (polyoxyethylene(9) octylphenyl ether)), to obtain an A-type mixture sample. Also, 150 μL of the solution obtained in (1) above by diluting the influenza B virus was added to 800 μL of the analyte extracting reagent, to obtain a B-type mixture sample.

(3) Then, 200 μL of the A-type mixture sample and the B-type mixture sample prepared in (2) above were taken into respective test tubes.

(4) Next, the test devices of FIG. 5A to 5C obtained by the above procedure were placed in the test tubes, respectively, prepared in (3) above.

(5) Then, after the test tubes were allowed to stand for a while with the test devices kept therein, measurements were carried out on items mentioned below. Table 2 shows the results. On the items mentioned below, Judgment was made by preparing a visual observation judgment specimen, in which 1+ is given to a line intensity of equal to or more than 0.015 and less than 0.03 measured by TSR 3000 membrane strip reader manufactured by BioDot Inc., 2+ is given to a line intensity of equal to or more than 0.03 and less than 0.08, 3+ is given to a line intensity of equal to or more than 0.08, and by referring to the

TABLE 1

| Distance (mm) | Sample receiving member (mm) | Label Holding Member (mm) | Chromatographic membrane (mm) | Absorption Member (mm) | Seal for Covering Sample receiving member (mm) | Seal for Covering Absorption Member (mm) | Remarks |
|---|---|---|---|---|---|---|---|
| −3 | 18 | 5 | 30 | 41 | 13 | 46 | See FIG. 5A |
| 0 | 21 | 5 | 30 | 41 | 16 | 46 | See FIG. 5B |
| 3 | 24 | 5 | 30 | 41 | 19 | 46 | See FIG. 5C |
| 5 | 26 | 5 | 30 | 41 | 21 | 46 | See FIG. 5C |
| 10 | 31 | 5 | 30 | 41 | 26 | 46 | See FIG. 5C |
| 20 | 41 | 5 | 30 | 41 | 36 | 46 | See FIG. 5C |

First, as shown in FIGS. 5A to 5C, to the substrate 1 made of a backing sheet, there were attached the chromatographic membrane 9 prepared in 1-1 above, the label holding member 5 prepared in 1-2 above, the sample receiving member 3 made of a nonwoven fabric (90% of cellulose and 10% of rayon), and the absorption member 11 made of a nonwoven fabric (cellulose). Next, transparent seals 13 and 15 were attached to cover the sample receiving member 3 and the absorption member 11, respectively, as shown in FIGS. 5A to 5C. Finally, the resulting substrate was cut into widths of 5 mm by a cutting device (manufactured by BioDot Inc.) Thus, preparation of the immunochromatographic test devices was completed.

visual observation judgment specimen to score in the intensities of lines that appeared on each test device.

(a) The time that elapsed before the background cleared (BG Clearance)

(b) The time that elapsed before elution of the latex particles from the label holding member was completed (Elution Time)

(c) The time that elapsed before the line intensity at the control zone 9C reached 3+

(d) The time that elapsed before the line intensity at the first detection zone 9A reached 1+

(e) The time that elapsed before the line intensity at the first detection zone 9A reached 2+

(f) The time that elapsed before the line intensity at the second detection zone 9B reached 1+

(g) The time that elapsed before the line intensity at the second detection zone 9B reached 2+

(h) Visual observation score in the first detection zone 9A and the second detection zone 9B after a set judgment time (10 min. after each test device was placed)

(i) The presence or absence of a rise in the background and the sensitivity after the set judgment time

TABLE 2

| Distance (mm) | BG Clearance (mm) | Elution Time (mm) | Control Zone 3+ | First Detection Zone 1+ | First Detection Zone 2+ | Second Detection Zone 1+ | Second Detection Zone 2+ | Judgment (After Lapse of 10 min.) First Detection Zone | Judgment (After Lapse of 10 min.) Second Detection Zone | Rise in BG and Sensitivity |
|---|---|---|---|---|---|---|---|---|---|---|
| −3 | 9 | 10< | 6 | 6 | 10< | 6 | 10< | 1+ | 1+ | in BG and Sensitivity |
| 0 | 9 | 10< | 5 | 5 | 10 | 5 | 10 | 2+ | 2+ | in BG and Sensitivity |
| 3 | 8 | 10< | 4 | 4 | 9 | 4 | 9 | 2+ | 2+ | in BG |
| 5 | 8 | 10 | 4 | 4 | 8 | 4 | 9 | 2+ | 2+ | No Rise |
| 10 | 7 | 9 | 4 | 3 | 6 | 3 | 7 | 2+ | 2+ | No Rise |
| 20 | 7 | 8 | 4 | 2 | 6 | 2 | 6 | 2+ | 2+ | No Rise |

3. Findings

Table 2 shows the following:

(1) The time that elapsed before the background cleared was shortened as the distance between the label holding member Sand the chromatographic membrane 9 was increased.

(2) The time that elapsed before elution of the latex particles from the label holding member 5 was completed was shortened as the distance between the label holding member 5 and the chromatographic membrane 9 was increased.

(3) The time that elapsed before lines at the control zone 9C, the first detection zone 9A and the second detection zone 9B appeared was shortened as the distance between the label holding member 5 and the chromatographic membrane 9 was increased.

(4) A rise in background and a rise in sensitivity achieved after the set judgment time (after the lapse of 10 min.) were lessened as the distance between the label holding member 5 and the chromatographic membrane 9 was increased, and a rise in a signal of each line to a set sensitivity within a set time was completed by providing a distance of 5 mm or more between the label holding member 5 and the chromatographic membrane 9.

From the above, it was experimentally confirmed that the use of the test device according to the present invention permits rapid yield of test results.

What is claimed is:

1. An immunochromatographic test device comprising:
   a sample receiving member for receiving a sample;
   a label holding member for holding a first labeling substance to bind to a first analyte contained in the sample; and
   a chromatographic membrane having a first detection zone at which a first immobilization substance to bind to the first analyte is immobilized, wherein the label holding member is laterally spaced apart from the chromatographic membrane, and the sample receiving member is disposed so as to cover the label holding member and to contact with the chromatographic membrane, and the labeling holding member is disposed so as to contact with the sample receiving member and not to contact with the chromatographic membrane.

2. The test device of claim 1, wherein the sample receiving member comprises a material which permits the sample to develop at a faster rate than the chromatographic membrane does.

3. The test device of claim 1, wherein the sample receiving member comprises a nonwoven fabric.

4. The test device of claim 1, wherein the sample receiving member and the label holding member comprise a nonwoven fabric.

5. The test device of claim 1, wherein the sample receiving member is made of rayon or a glass fiber, and the chromatographic membrane is made of nitrocellulose.

6. The test device of claim 1, wherein the first labeling substance comprises colored latex particles and an antibody to bind to the first analyte.

7. The test device of claim 1, wherein the label holding member further comprises a second labeling substance to bind to a second analyte contained in the sample, and the chromatographic membrane further comprises a second detection zone at which a second immobilization substance to bind to the second analyte is immobilized.

8. The test device of claim 7, wherein the first labeling substance, the second labeling substance, the first immobilization substance and the second immobilization substance comprise antibodies.

9. The test device of claim 7, wherein the second labeling substance comprises colored latex particles and an antibody to bind to the second analyte.

10. The test device of claim 1, wherein the label holding member holds a control labeling substance, and the chromatographic membrane has a control zone at which a control immobilization substance capable of binding to the control labeling substance is immobilized.

11. The test device of claim 10, wherein the control labeling substance comprises colored latex particles.

12. The test device of claim 10, wherein the control labeling substance comprises avidin, and the control immobilization substance comprises biotin.

13. The test device of claim 10, wherein the control labeling substance comprises biotin, and the control immobilization substance comprises avidin.

14. The test device of claim 1, further comprising an absorption member which is disposed in contact with the chromatographic membrane.

15. The test device of claim 14, wherein the absorption member comprises a nonwoven fabric and is made of cellulose.

16. An immunochromatographic test device comprising:
a label holding member for holding a labeling substance to bind to an analyte contained in a sample;
a chromatographic membrane having a detection zone at which an immobilization substance to bind to the analyte is immobilized;
an elongated sample receiving member having
a sample receiving part for receiving the sample,
a covering part for covering the label holding member, and
a contacting part for contacting the chromatographic membrane; and
an elongated substrate for supporting the sample receiving part of the elongated sample receiving member, the label holding member, and the chromatographic membrane, wherein
the label holding member and the chromatographic membrane are spaced apart on the substrate,
the elongated sample receiving member is arranged so that the sample receiving part is arranged adjacent to the label holding member on the substrate, and
the covering part covers the label holding member and the contacting part contacts with the chromatographic membrane.

17. The test device of claim 16, wherein the elongated sample receiving member comprises a second contacting part which is arranged on the substrate so as to contact with the substrate between the label holding member and the chromatographic membrane.

18. The test device of claim 17, wherein the sample receiving part, the label holding member covered by the covering part, the second contacting part, the contacting part, and the chromatographic membrane are arranged on the substrate in order of upstream to downstream direction of the sample development so that the sample is developed by capillarity.

* * * * *